United States Patent
Michlig Gonzalez et al.

(10) Patent No.: US 9,867,790 B2
(45) Date of Patent: Jan. 16, 2018

(54) COMPOSITIONS AND METHODS USING CUMINALDEHYDE

(71) Applicant: NESTEC S.A., Vevey (CH)

(72) Inventors: Stephanie Michlig Gonzalez, Le Mont-sur-lausanne (CH); Jenny Meylan Merlini, Lausanne (CH); Susana Camacho, Lausanne (CH); Johannes Le Coutre, Pully (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/907,124

(22) PCT Filed: Jul. 18, 2014

(86) PCT No.: PCT/EP2014/065473
§ 371 (c)(1),
(2) Date: Jan. 22, 2016

(87) PCT Pub. No.: WO2015/011037
PCT Pub. Date: Jan. 29, 2015

(65) Prior Publication Data
US 2016/0151304 A1   Jun. 2, 2016

Related U.S. Application Data

(60) Provisional application No. 61/857,051, filed on Jul. 22, 2013.

(51) Int. Cl.
*A61K 31/11*   (2006.01)
*A23L 33/10*   (2016.01)

(52) U.S. Cl.
CPC ........... *A61K 31/11* (2013.01); *A23L 33/10* (2016.08)

(58) Field of Classification Search
None
See application file for complete search history.

(56) References Cited

U.S. PATENT DOCUMENTS

| | | |
|---|---|---|
| 2009/0263514 A1 | 10/2009 | Gopinathan |
| 2010/0159028 A1 | 6/2010 | Shultz |
| 2012/0189734 A1 | 7/2012 | Tek et al. |

FOREIGN PATENT DOCUMENTS

| | | | |
|---|---|---|---|
| CN | 102106999 | * | 6/2011 |
| JP | 1042826 | | 2/1998 |
| JP | 2010083796 | | 4/2010 |
| KR | 20030090396 | | 11/2003 |

OTHER PUBLICATIONS

Rofes et al. (J of Gastroenterology and Hepatology Research, 3(5), 2014).*
PDF regardiing dysphagia from Mayoclinic (2016).*
PDF regardiing dysphagia from NHS (2016).*
English translation of CN-102106999 (Specification only), 2011.*
Lee "Cuminaldehyde: Aldose Reductase and α-Glucosidase Inhibitor Derived from Cuminum cyminum L. Seeds" Journal of Agricultural and Food Chemistry, 2005, vol. 53, pp. 2446-2450.
Kalia et al. "Hypoglycemic and insulin release effects of cuminaldehyde: A new hypoglycemic natural compound from cumin oil" Journal of Science and Pharmacy, 2005, vol. 6, No. 2, pp. 45-47.

* cited by examiner

*Primary Examiner* — Bong-Sook Baek
(74) *Attorney, Agent, or Firm* — K&L Gates LLP

(57) ABSTRACT

Compositions contain a therapeutically effective amount of cuminaldehyde for at least one of provoking the swallowing reflex of dysphagic patients, decreasing appetite by delaying gastric emptying, reducing body weight gain, or reducing gylcemia by improving insulin sensitivity or improving mood, memory or cognition. Methods are provided that include administering such compositions.

5 Claims, 7 Drawing Sheets

COMPOSITIONS AND METHODS USING CUMINALDEHYDE

CROSS REFERENCE TO RELATED APPLICATIONS

The present application is a National Stage of International Application No. PCT/EP2014/065473, filed on Jul. 18, 2014, which claims priority to U.S. Provisional Application Serial No. 61/857,051, filed Jul. 22, 2013, the entire contents of which are being incorporated herein by reference.

BACKGROUND

The present disclosure generally relates to compositions comprising a naturally-occurring compound. More specifically, the present disclosure relates to compositions comprising cuminaldehyde and further relates to methods comprising administering such compositions.

Dysphagia is a condition typified by a decreased ability to swallow. The normal swallow involves three distinct phases which are interdependent and well coordinated: the oral, the pharyngeal, and the esophageal phases. In the oral phase, which is under voluntary control, food that has been chewed and mixed with saliva is formed into a bolus for delivery by voluntary tongue movements to the back of the mouth, into the pharynx. The pharyngeal phase is involuntary and is triggered by the food/liquid bolus passing through the faucial pillars into the pharynx. Contraction of the three constrictors of the pharynx propels the bolus towards the upper oesophageal sphincter. Simultaneously, the soft palate closes the nasopharynx. The larynx moves upwards to prevent food or liquid passing into the airway, which is aided by the backward tilt of the epiglottis and closure of the vocal folds. The oesophageal phase is also involuntary and starts with the relaxation of the upper oesophageal sphincter followed by peristalsis, which pushes the bolus down to the stomach.

Esophageal dysphagia affects a large number of individuals of all ages, but is generally treatable with medications and is considered a less serious form of dysphagia. Oral pharyngeal dysphagia, on the other hand, is a very serious condition and is generally not treatable with medication. Oral pharyngeal dysphagia also affects individuals of all ages, but is more prevalent in older individuals. Worldwide, oral pharyngeal dysphagia affects approximately 22 million people over the age of 50.

The consequences of untreated or poorly managed oral pharyngeal dysphagia can be severe, including dehydration, malnutrition, airway obstruction with solid foods (choking), and airway aspiration of liquids and semi-solid foods, promoting aspiration pneumonia and/or pneumonitis. Severe oral pharyngeal dysphagia may require nutrition to be supplied by tube feeding. Mild to moderate oral pharyngeal dysphagia requires the texture of foods to be modified in order to minimize the likelihood of choking or aspiration.

Improving an individual's ability and efficiency to swallow improves the individual's safety through reduced risk of pulmonary aspiration. An efficient swallow may permit greater independence from feeding assistance and/or reduced length of time spent in feeding-assistance during meal consumption. Efficient swallow also reduces the viscosity of liquids required for safety (e.g., pudding, honey and nectar thickness products) and may also limit the use of texture-modified foods. All of these previously described factors are aimed at improving an individual's quality of life.

Research on the molecular mechanisms underlying pungent sensations revealed the existence of two cation channels, TRPV1 (transient receptor potential V1) and TRPA1 (transient receptor potential A1) that are expressed in the somatosensory fibers innervating the oral cavity. TRPV1 is the receptor for heat and burning sensations such as capsaicin, the hot molecule in red hot chili peppers. TRPA1 responds to cold and pungent compounds such as allyl isothiocyanate (mustard oil) and cinnamaldehyde (cinnamon). At moderated concentrations, TRPA1 agonists exhibit a pleasant tingling sensation.

Although oral administration of capsaicin has been shown to promote a swallow reflex, capsaicin is a particularly pungent and toxic compound. Physiological effects associated with oral administration of capsaicin include a burning sensation of heat from the mid-tongue to the throat, shortness of breath, fainting, nausea, and spontaneous vomiting. Mustard oil is similarly pungent, and cinnamaldehyde is tingling. As a result, only small quantities of capsaicin, mustard oil or cinnamaldehyde may be administered without causing discomfort to the individual. Food products containing capsaicin, mustard oil or cinnamaldehyde are frequently not accepted by the consumer as providing a very unpleasant mouth feeling. In particular, both the tingling and burning effect are considered to be very unsavory affecting the consumption of the food product.

Another condition adversely affecting some individuals is that their body tissues do not respond properly to insulin. Insulin receptors in the tissues cease to function adequately and gluco-dependant cells fail to recognize the presence of insulin. As a result, the pancreas needs to secrete more insulin to help glucose enter these cells. The pancreas tries to keep up with this increased demand for insulin by producing more. This phenomenon is called insulin resistance (also known as low insulin sensitivity). Many people with insulin resistance have high levels of both glucose and insulin circulating in their blood at the same time. Eventually, the pancreas fails to keep up with the body's need for insulin, leading to Type II diabetes.

Insulin resistance and Type II diabetes are associated to increased risk of heart attacks, strokes, amputation, diabetic retinopathy, and kidney failure. For extreme cases, circulation of limbs is affected, potentially requiring amputation. Loss of hearing, eyesight, and cognitive ability has also been linked to these conditions Management of insulin resistance in children and adults is essentially based on dietary and lifestyle changes, including healthier dietary habits and increased exercise. These practices can be very efficient in improving insulin sensitivity and in slowing the progression of the disease, but they are difficult to apply and actually not followed by most patients. Type II diabetes can be treated with drugs promoting insulin sensitivity, but their efficacy in reducing the rate of progression of the disease is quite low. Insulin treatment is required during the most advanced phases of the disease.

Products containing n-3 polyunsaturated fatty acids, fibers, oligosaccharides and even probiotics have been proposed as nutritional solutions to improve insulin sensitivity and to reduce insulin resistance. However, the efficacy of these nutritional interventions is quite marginal and even controversial, with studies showing no or even deleterious effects.

Yet another condition adversely affecting some individuals is obesity. The prevalence of obesity has increased worldwide to epidemic proportion. Approximately 1 billion of people worldwide are overweight or obese, conditions that increase mortality, mobility and economical costs. Obesity develops when energy intake is greater than energy expenditure, the excess energy stored mainly as fat in adipose tissue. Body weight loss and prevention of weight gain can be achieved by reducing energy intake or bioavailability, increasing energy expenditure and/or reducing storage as fat. However, overweight subjects or subjects at risk of becoming overweight often need nutritional assistance for better managing their body weight, e.g. through increasing satiety and/or reducing body weight gain.

Yet another condition adversely affecting some individuals is impaired neurotransmission, for example low levels of neurotransmitters such as epinephrine. Impaired neurotransmission is connected to mood disorders such as depression, anxiety disorders, and increased susceptibility to stress, and also connected to cognitive dysfunction.

Carbohydrate-rich foods are known for providing important metabolic fuel for physical performance, but their effects on mood and cognitive performance are not very clear. However, irritability and aggression are influenced by individual differences in insulin release, the frequency that meals are eaten, and the effect of these meals on blood glucose values. Benton, "Carbohydrate ingestion, blood glucose and mood," Neuroscience and Biobehavioral Reviews, 26:293-308 (2002). Furthermore, the ability to control the levels of blood glucose is related to both mood and cognition. For example, in a study in which participants were given an oral glucose tolerance test and cognitive tests, the older age group showed that those with poorer glucose tolerance forgot more words and had slower decision times; and, in those participants with poor glucose tolerance, a tendency for blood glucose to fall below baseline values was associated with better mood and faster working memory. Young and Benton, "The nature of the control of blood glucose in those with poorer glucose tolerance influences mood and cognition," Metab. Brain Dis. (Mar. 26, 2014).

SUMMARY

The present inventors surprisingly and unexpectedly found that cuminaldehyde is an agonist of the cation channel TRPA1 and activates TRPA1 at an efficacy of 140% relative to a known TRPA1 agonist, cinnamaldehyde. Moreover, compared to mustard-derived potent agonists such as ally isothiocianate, cuminaldehyde is not an irritant. Without wishing to be bound by theory, the present inventors believe that activation of TRPA1 is effective to 1) help to provoke the swallowing reflex of dysphagic patients, 2) decrease appetite by delaying gastric emptying, 3) reduce body weight gain, and 4) reduce gylcemia by improving insulin sensitivity or glucose tolerance, 5) improve mood, memory or cognition. Cuminaldehyde is described as having spicy with green cumin and herbal nuances (Fenaroli's Handbook of Flavor Ingredients, sixth edition), making it more pleasant compared to other TRPA1 agonists.

Accordingly, in a general embodiment, the present disclosure provides a method of treating dysphagia. The method comprises administering to an individual having the dysphagia a composition comprising a therapeutically effective amount of cuminaldehyde.

In a related embodiment, the dysphagia is oral pharyngeal dysphagia.

In a related embodiment, the composition is a thickened beverage.

In a related embodiment, the therapeutically effective amount of cuminaldehyde provokes a swallowing reflex.

In a related embodiment, the cuminaldehyde is in a form selected from the group consisting of isolated cuminaldehyde and synthetic cuminaldehyde.

In another embodiment, a method of decreasing appetite is provided. The method comprises administering to an individual in need thereof a composition comprising cuminaldehyde in an amount therapeutically effective for delaying gastric emptying.

In a related embodiment, the individual has a condition selected from the group consisting of overweight, obesity, a risk of overweight, a risk of obesity, and combinations thereof.

In another embodiment, a method of reducing body weight gain is provided. The method comprises administering to an individual in need thereof a composition comprising a therapeutically effective amount of cuminaldehyde.

In a related embodiment, the individual has a condition selected from overweight, obesity and a combination thereof.

In another embodiment, a method of reducing glycemia is provided. The method comprises administering to an individual in need thereof a composition comprising cuminaldehyde in an amount therapeutically effective for improving insulin sensitivity or glucose tolerance, mood or memory.

In a related embodiment, the individual is selected from the group consisting of an infant born preterm, an infant experiencing intrauterine growth restriction, a pregnant woman suffering from gestational diabetes, a human suffering from insulin resistance, and a human suffering from type II diabetes.

In another embodiment, a composition is provided. The composition comprises an amount of cuminaldehyde that is therapeutically effective for at least one of provoking the swallowing reflex of dysphagic patients, decreasing appetite by delaying gastric emptying, reducing body weight gain, or reducing glycemia by improving insulin sensitivity or glucose tolerance or improving mood or memory or cognition.

In a related embodiment, the composition is a food product. The food product can comprise a component selected from the group consisting of protein, carbohydrate, fat and combinations thereof.

In another embodiment, the present disclosure provides a method for improving one or more of cognitive performance, cognition, mood, or memory comprising administering to an individual in need thereof a composition comprising a therapeutically effective amount of cumminaldehyde In an embodiment, the individual has a condition selected from the group consisting of cognitive decline, mild cognitive impairment, dementia, a mood disorder, memory loss, and combinations thereof.

In another embodiment, a method of making a nutritional composition is provided. The method comprises incorporating into the nutritional composition an amount of cuminaldehyde that is therapeutically effective for at least one of provoking the swallowing reflex of dysphagic patients, decreasing appetite by delaying gastric emptying, reducing body weight gain, or reducing glycemia by improving insulin sensitivity or glucose tolerance or improving mood or memory.

An advantage of the present disclosure is to use a TRPA1 agonist that is more pleasantly consumed relative to other TRPA1 agonists.

Another advantage of the present disclosure is to use a naturally-occurring compound to prevent aspiration pneumonia in dysphagic patients and/or trigger the swallowing reflex of a dysphagic patient.

Still another advantage of the present disclosure is use a naturally-occurring compound to decrease appetite by delaying gastric emptying.

Yet another advantage of the present disclosure is to use a naturally-occurring compound to reduce body weight gain.

An additional advantage of the present disclosure is to use a naturally-occurring compound to reduce gylcemia by improving insulin sensitivity or glucose tolerance.

Another advantage of the present disclosure is to treat dysphagia with tolerable side effects or no side effects.

Still another advantage of the present disclosure is to promote safe swallowing of a food bolus.

Yet another advantage of the present disclosure is to use a TRPA1 agonist that is more tolerably consumed than mustard derived potent agonists such as ally isothiocianate.

An additional advantage of the present disclosure is to use a TRPA1 agonist that has increased efficacy relative to the powerful agonist cinnamaldehyde.

Still another advantage of the present disclosure is to improve at least one of mood, memory or cognition.

Still another advantage of the present disclosure is to improve at least one of mood, memory or cognition with a compound that can be easily and safely used in food products.

An additional advantage of the present disclosure is to improve at least one of mood, memory or cognition with a naturally-occurring compound that can be found in spices.

Another advantage of the present disclosure is to improve at least one of mood, memory or cognition with tolerable side effects or no side effects.

Yet another advantage of the present disclosure is to improve at least one of mood, memory or cognition with a compound that has increased acceptability, reduced pungency, and improved tolerance in the gastrointestinal tract relative to capsaicin.

Additional features and advantages are described herein, and will be apparent from, the following Detailed Description and the Figures.

DETAILED DESCRIPTION

Figure 2:
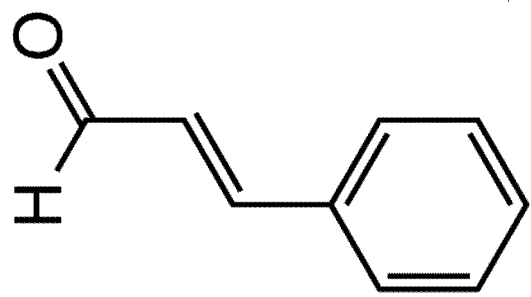
FIG. 2 shows the chemical structure of cinnamaldehyde.

All percentages expressed herein are by weight of the total weight of the composition unless expressed otherwise. When reference is made to the pH, values correspond to pH measured at 25° C. with standard equipment. As used in this disclosure and the appended claims, the singular forms "a," "an" and "the" include plural referents unless the context clearly dictates otherwise. As used herein, "about" is understood to refer to numbers in a range of numerals. Moreover, all numerical ranges herein should be understood to include all integers, whole or fractions, within the range.

As used herein, "comprising," "including" and "containing" are inclusive or open-ended terms that do not exclude additional, unrecited elements or method steps. However, the beverages provided by the present disclosure may lack any element that is not specifically disclosed herein. Thus, any embodiment defined herein using the term "comprising" also includes embodiments "consisting essentially of" and "consisting of" the disclosed components.

"Prevention" includes reduction of risk and/or severity of a disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measures. The terms "treatment," "treat" and "alleviate" are further intended to include the dietary management of a disease or condition or the dietary management for prophylaxis or prevention a disease or condition. A treatment can be patient-or doctor-related.

As used herein, a "therapeutically effective amount" is an amount that prevents a deficiency, treats a disease or medical condition in an individual or, more generally, reduces symptoms, manages progression of the diseases, or provides a nutritional, physiological, or medical benefit to the individual.

"Animal" includes, but is not limited to, mammals, which includes but is not limited to, rodents, aquatic mammals, domestic animals such as dogs and cats, farm animals such as sheep, pigs, cows and horses, and humans. Where "animal," "mammal" or a plural thereof is used, these terms also apply to any animal that is capable of the effect exhibited or intended to be exhibited by the context of the passage. As used herein, the term "patient" is understood to include an animal, especially a mammal, and more especially a human that is receiving or intended to receive treatment, as treatment is herein defined. While the terms "individual" and "patient" are often used herein to refer to a human, the present disclosure is not so limited. Accordingly, the terms "individual" and "patient" refer to any animal, mammal or human, having or at risk for a medical condition that can benefit from the treatment.

"Food product" and "food composition," as used herein, are understood to include any number of optional additional ingredients, including conventional food additives, for example one or more proteins, carbohydrates, fats, acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

The present inventors tested cinnamaldehyde (chemical structure shown in FIG. 2) in mouse models. Cinnamaldehyde is a $\alpha,\beta$-unsaturated aldehyde that activates TRPA1, but not TRPV1 or TRPM8, with an EC50 of approximately 60 µM. Like mustard oil, cinnamaldehyde interacts with TRPA1 in a covalent manner.

Figure 3:
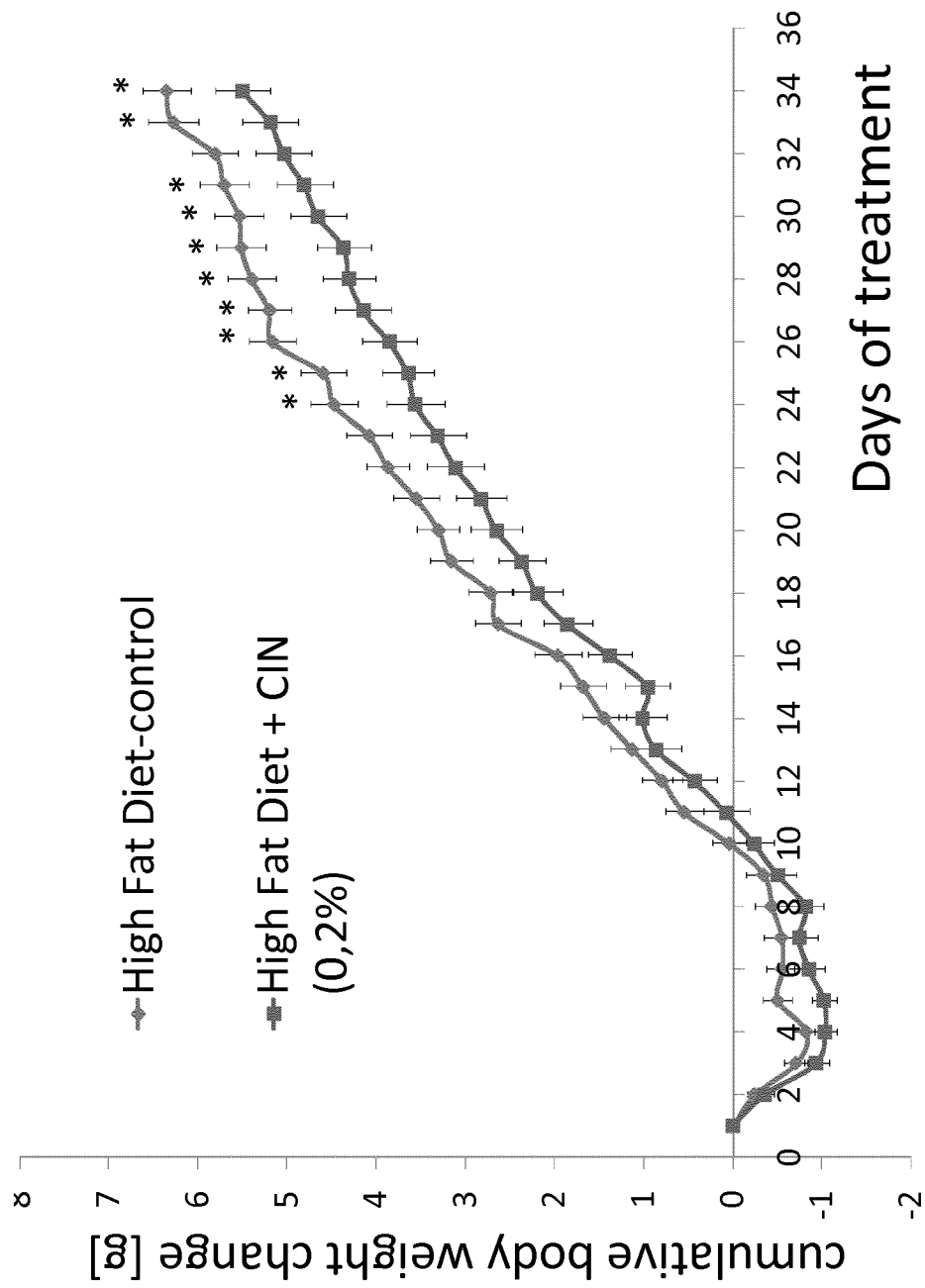
FIG. 3 shows a chart of body weight gain in mice with chronic ingestion of cinnamaldehyde or control.
Figure 4:
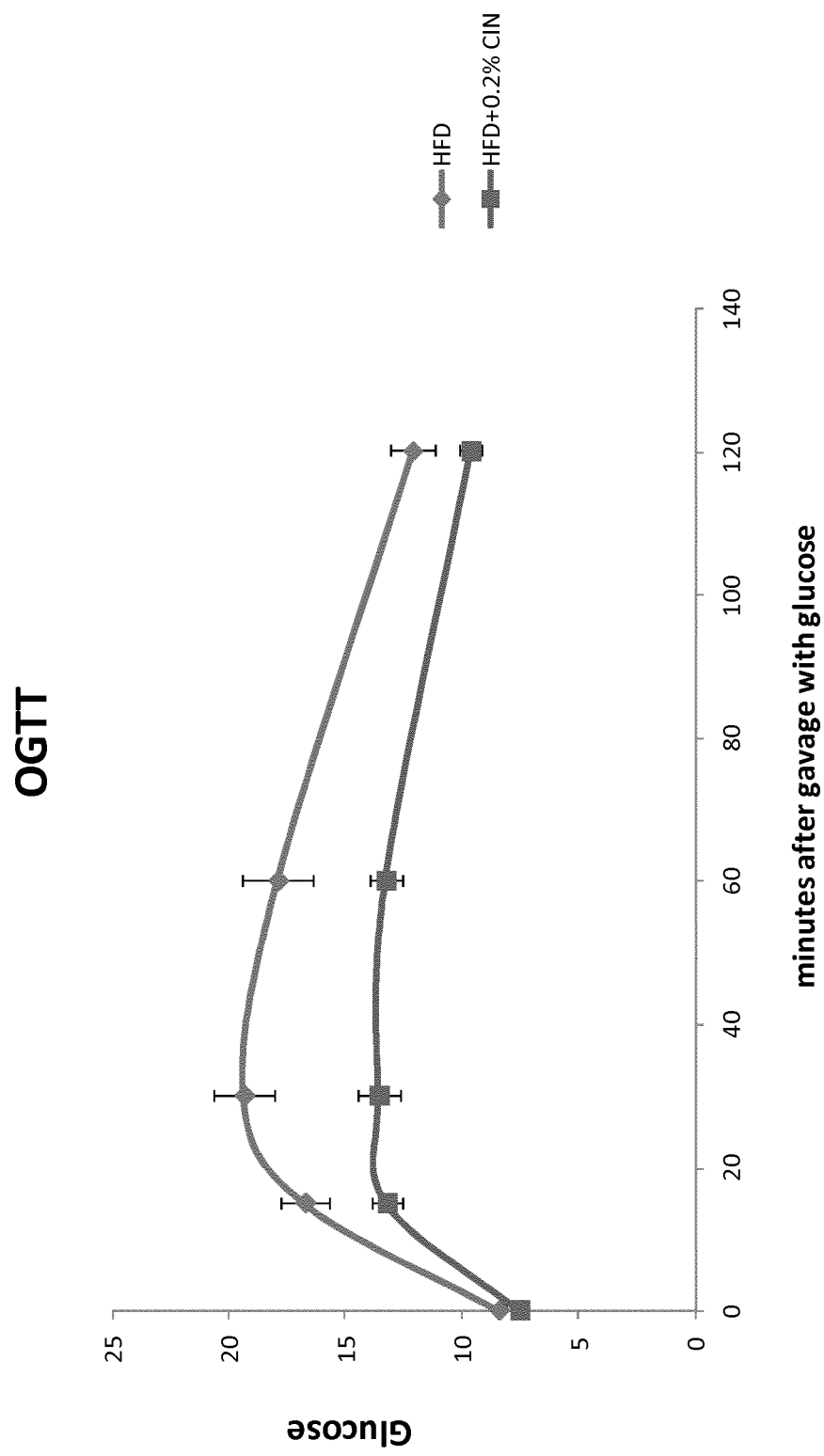
FIG. 4 shows a chart of insulin sensitivity in mice with chronic ingestion of cinnamaldehyde or control.
Figure 5:
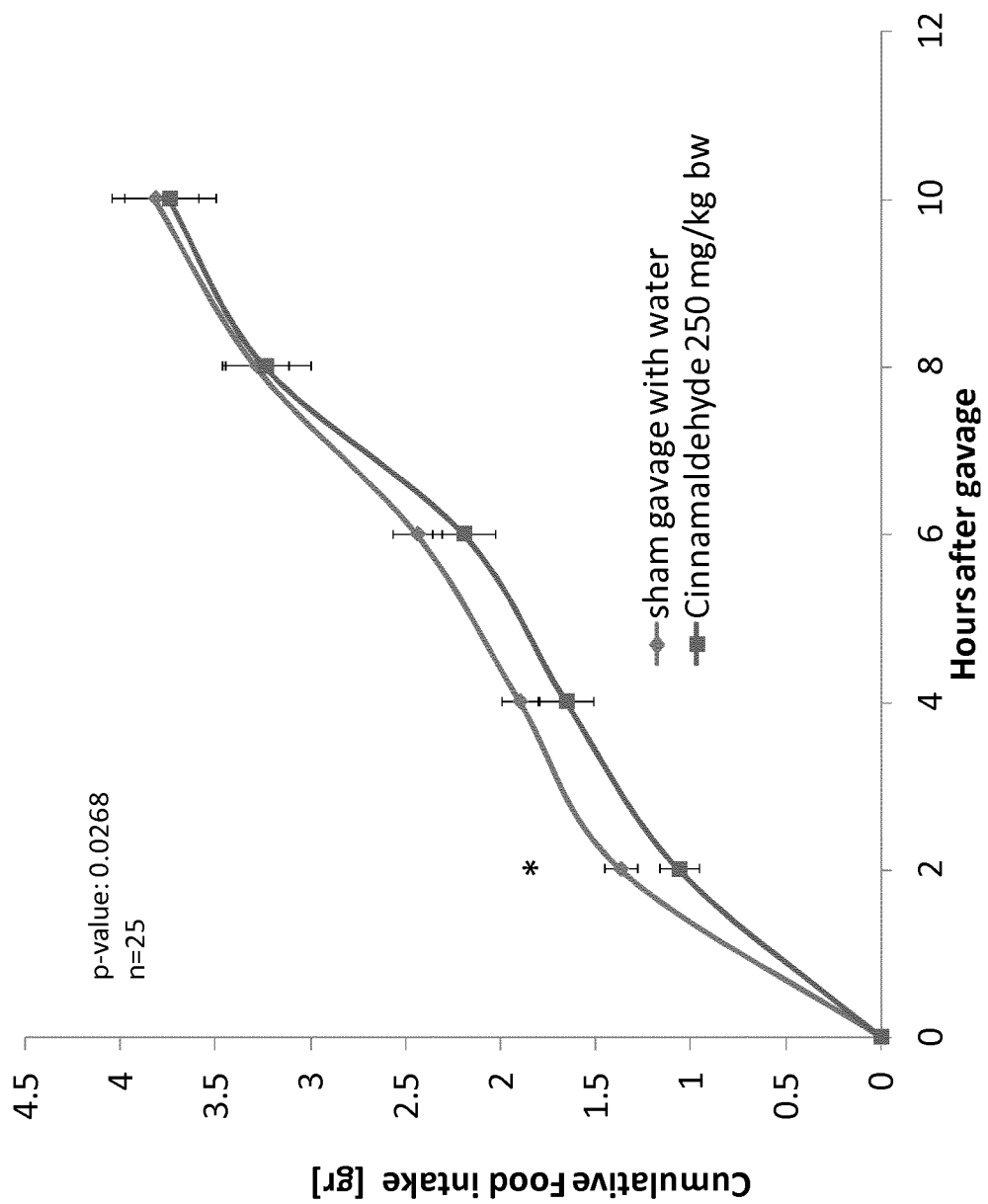
FIG. 5 shows a chart of short term food intake gain after a single cinnamaldehyde or control ingestion in mice.
Figure 6:
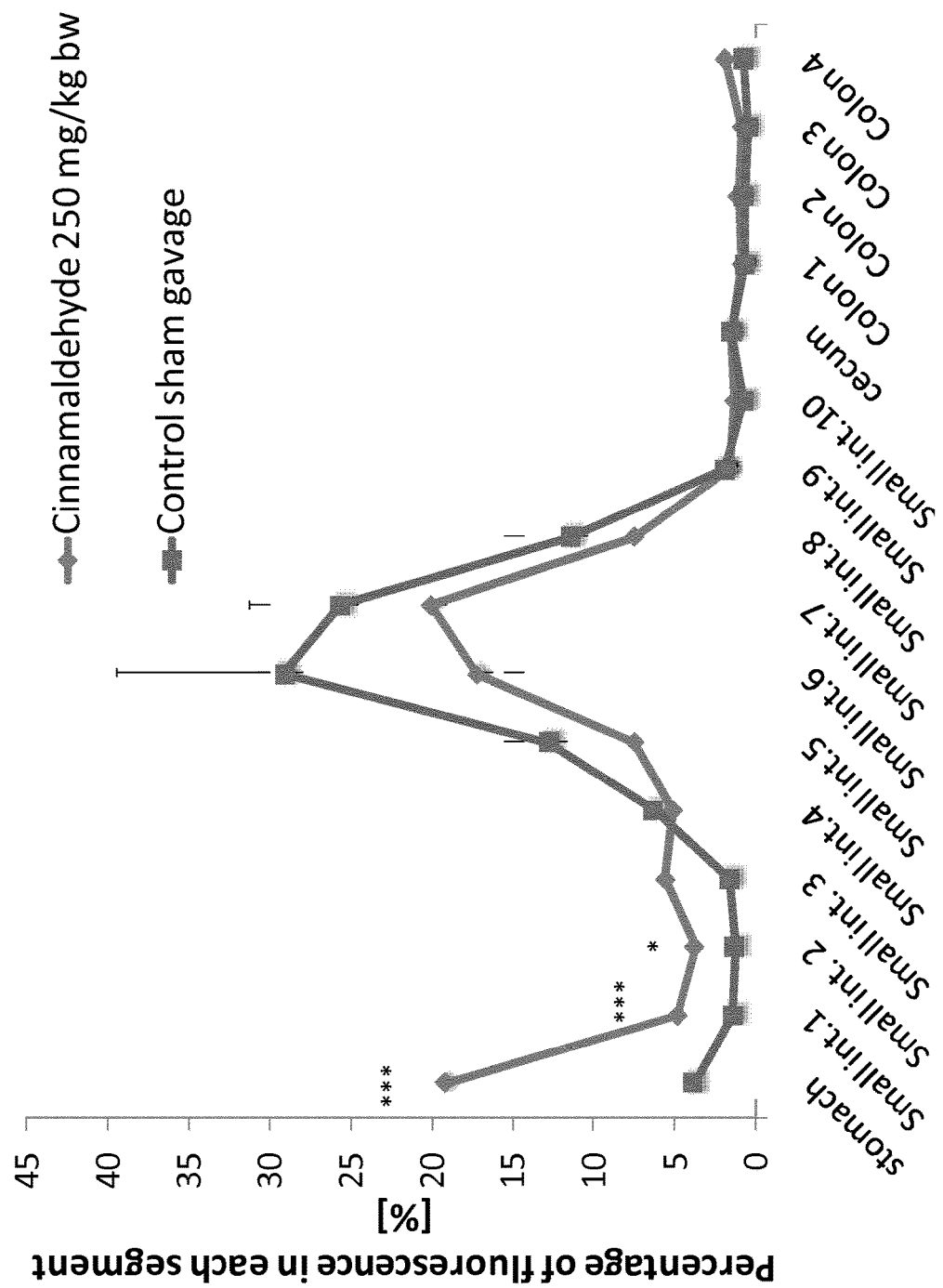
FIG. 6 shows a chart of gastric emptying after a single cinnamaldehyde or control ingestion in mice.

As shown in FIG. 3, mice chronically fed a high fat diet containing 0.2 wt % cinnamaldehyde gained less weight than mice fed the same high fat diet without cinnamaldehyde. As shown in FIG. 4, mice chronically fed a high fat diet containing 0.2 wt % cinnamaldehyde had improved insulin sensitivity relative to mice fed the same high fat diet without cinnamaldehyde. As shown in FIG. 5, mice fed a single dose of cinnamaldehyde had a reduction in short term food intake after the administration relative to mice fed a sham gavage. As shown in FIG. 6, mice fed a single dose of cinnamaldehyde had delayed gastric emptying after the administration relative to mice fed a sham gavage.

Figure 1:
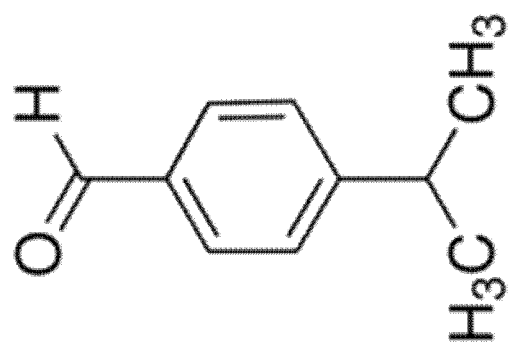
FIG. 1 shows the chemical structure of cuminaldehyde.
Figure 7:
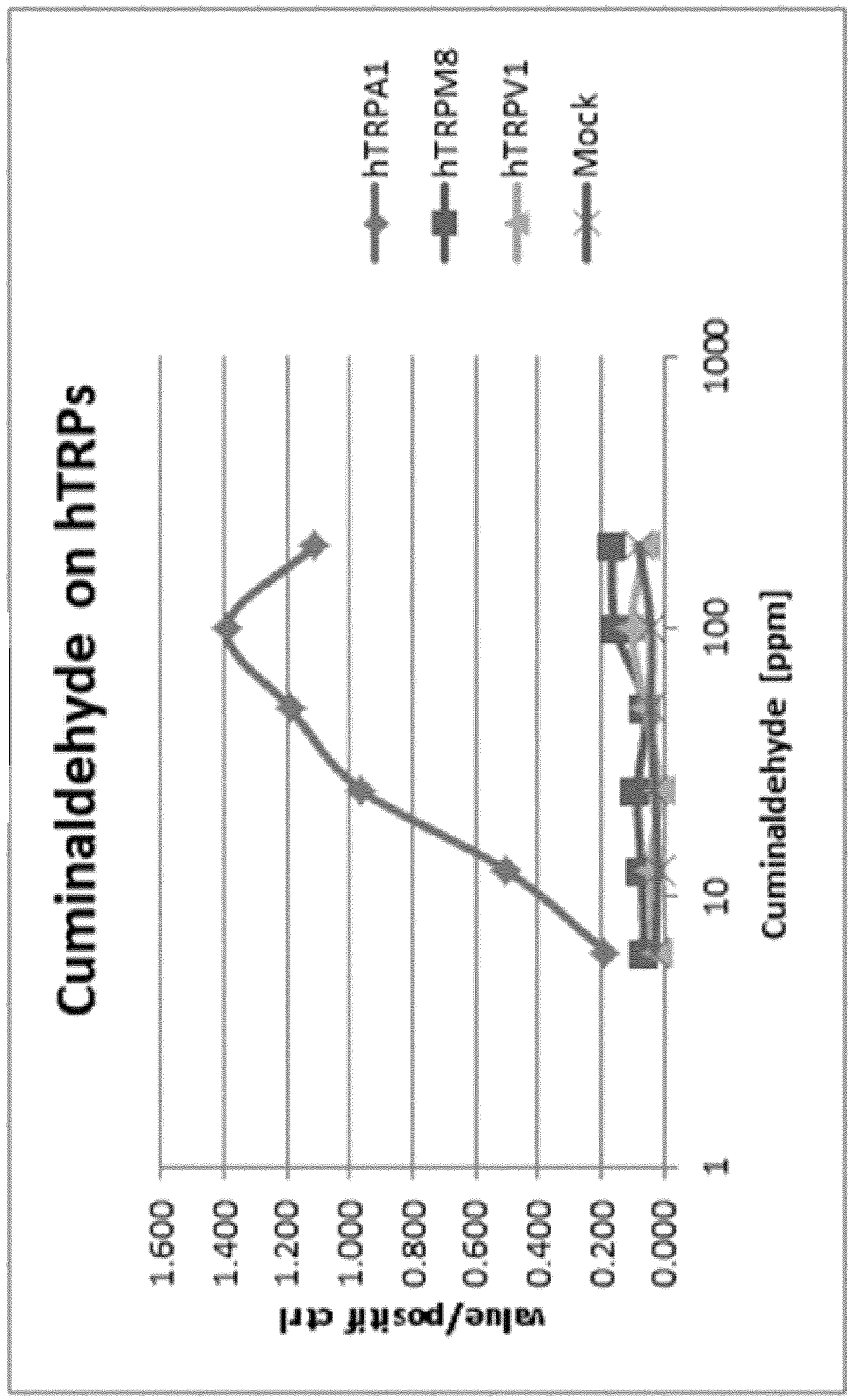
FIG. 7 shows the in vitro effect of cuminaldehyde on cell expression of TRP channels.

As noted above, the present inventors surprisingly and unexpectedly found that cuminaldehyde (chemical structure shown in FIG. 1) is an agonist of the cation channel TRPA1 and activates TRPA1 at an efficacy of 140% relative to a known TRPA1 agonist, cinnamaldehyde. FIG. 7 shows experimental data demonstrating that cuminaldehyde activates TRPA1.Cuminaldehyde activated TRPA1 (diamonds) in a dose-dependent fashion, and no activation was observed on TRPV1 (triangles), hTRPM8 (squares) and "empty" cells (-><-).

Figure 8A:
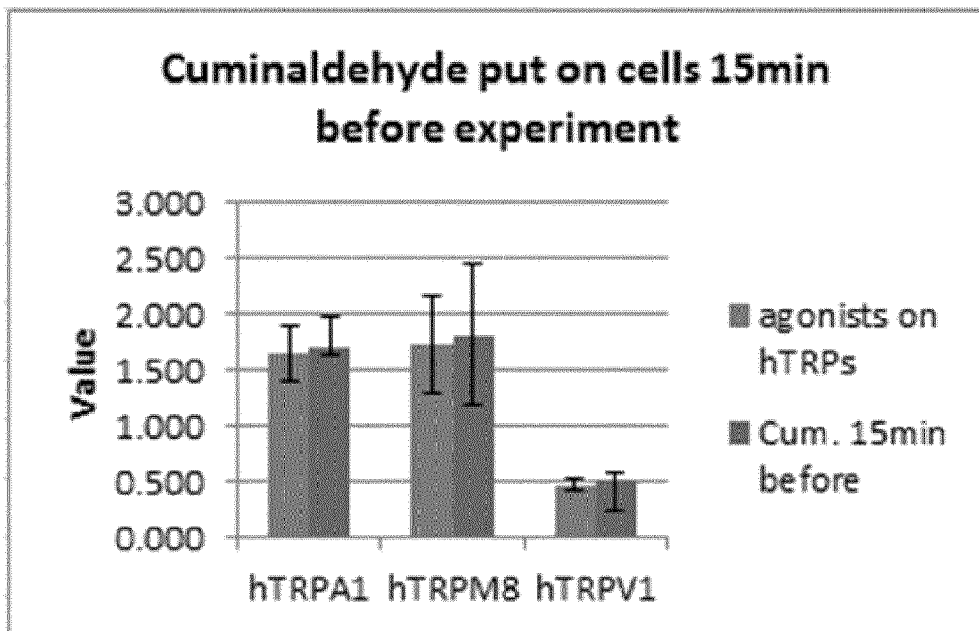
FIG. 8A shows the in vitro effect of cuminaldehyde pretreatment on cell expression of TRP channels as raw values.
Figure 8B:
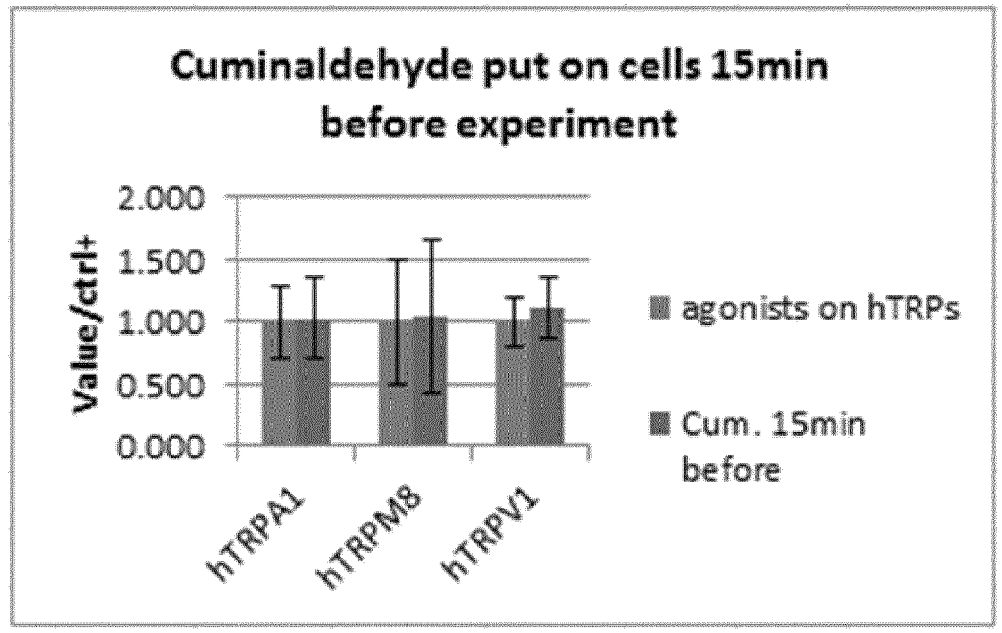
FIG. 8B shows the in vitro effect of cuminaldehyde pretreatment on cell expression of TRP channels as percentage of control.

FIGS. 8A and 8B demonstrate that cuminaldehyde does not desensitize the TRPA1, TRPV1 or TRPM8 cation channels when applied to cells fifteen minutes before the corresponding specific agonist. Specifically, cuminaldehyde was applied to cells fifteen minutes before cinnamaldehyde, icilin and capsaicin, which are specific agonists for TRPA1, TRPM8 and TRPV1 cation channels, respectively. After specific agonist application, the cation channel expression was measured. FIG. 8A shows the raw values of channel expression with or without cuminaldehyde pretreatment, and FIG. 8B shows the values as a percentage of the control lacking cuminaldehyde pretreatment. The left bars in each graph represent the controls lacking cuminaldehyde pretreatment, the right bars in each graph represent the samples including cuminaldehyde pretreatment. Each cation channel showed substantially similar results for cuminaldehyde pretreatment relative to control, so cuminaldehyde does not desensitize the TRPA1, TRPV1 or TRPM8 cation channels when applied to cells fifteen minutes before the corresponding specific agonist.

Due to the unexpected discovery that cuminaldehyde is also an agonist of the cation channel TRPA1, the present inventors believe that cuminaldehyde can activate TRPA1 similarly to cinnamaldehyde, but without the tingling irritant sensation, to 1) help to provoke the swallowing reflex of dysphagic patients, 2) decrease appetite and/or increase satiety by delaying gastric emptying, 3) reduce body weight gain, and 4) reduce gylcemia by improving insulin sensitivity or glucose tolerance. Accordingly, the present disclosure provides a composition comprising a therapeutically effective amount of cuminaldehyde for provoking the swallowing reflex of a dysphagic patient, decreasing appetite by delaying gastric emptying, reducing body weight gain, and/or reducing gylcemia by improving insulin sensitivity or glucose tolerance. In an embodiment, the cuminaldehyde can be an isolated compound, such as cuminaldehyde isolated from essential oils, cumin, cinnamon, bitter orange, and/or anise. In an embodiment, the cuminaldehyde can be synthetic cuminaldehyde.

In an embodiment, dysphagia is treated by administering to an individual having the dysphagia the composition comprising a therapeutically effective amount of cuminaldehyde. The dysphagia can be oral pharyngeal dysphagia and can be a consequence of at least one of surgery for oral cancer, surgery for throat cancer, a stroke, a brain injury, or a progressive neuromuscular disease, such as Parkinson's disease.

In another embodiment, the composition comprising a therapeutically effective amount of cuminaldehyde is administered to an infant (a child under the age of 12 months) born preterm and/or experiencing intrauterine growth restriction (IUGR), a pregnant woman suffering from gestational diabetes; or a child, an adolescent, or an adult suffering from insulin resistance and/or type II diabetes, such as an animal such as a human. The composition can reduce glycemia by improving insulin sensitivity or glucose tolerance in the subject.

In yet another embodiment, the composition is administered to an overweight or obese subject or to a subject at risk for becoming overweight or obese. "Overweight" is defined for an adult human as having a BMI between 25 and 30. Thereby, BMI (body mass index) means the ratio of weight in kilograms divided by the height in meters squared; or the ratio of weight in pounds divided by the height in inches squared, multiplied by 703. "Obesity" is a condition in which the natural energy reserve, stored in the fatty tissue of animals, in particular humans and other mammals, is increased to a point where it is associated with certain health conditions or increased mortality. "Obese" is defined for a human as having a BMI greater than 30. The composition can decrease appetite by delaying gastric emptying and/or reduce body weight gain in the subject. In an embodiment, the subject is a non-overweight and/or non-obese individual avoiding weight gain.

The composition is in an administrable form which is preferably selected from the group consisting of pharmaceutical formulations, nutritional formulations, dietary supplements, functional food and beverage products, and combinations thereof. The present disclosure provides a method of making a nutritional composition that includes incorporating a therapeutically effective amount of cuminaldehyde into the nutritional composition. The cuminaldehyde incorporated into the nutritional composition can be in the form of isolated cuminaldehyde.

As noted above, there is a direct link between glucose tolerance and mood, memory and cognition. For example, in a study in which participants were given an oral glucose tolerance test and cognitive tests, the older age group showed that those with poorer glucose tolerance forgot more words and had slower decision times; and, in those participants with poor glucose tolerance, a tendency for blood glucose to fall below baseline values was associated with better mood and faster working memory. See, e.g., Young and Benton (2014). Therefore, without being bound by theory, the inventors believe that cuminaldehyde enhances insulin sensitivity and/or glucose tolerance and can thereby improve one or more of mood, memory or cognition.

Accordingly, in an embodiment, the composition comprising cuminaldehyde can be administered in a method of improving one or more of cognitive performance, cognition, mood or memory in an individual in need thereof The composition can treat or prevent one or more of cognitive decline, mild cognitive impairment, dementia, a mood disorder, or memory loss in an individual having one or more of these conditions. The composition can be administered at least once a day for at least one week, preferably at least one month, and more preferably at least one year. The composition can be administered to an infant (a child under the age of twelve months), a child (up to twelve years of age), an adolescent (twelve to eighteen years of age), an adult (over eighteen years of age), or an elderly individual (past the first two thirds of the average expected lifespan in its country of origin, preferably past the first three quarters of the average expected lifespan in its country of origin; an elderly human is a person with a chronological age of 65 years or older).

Cognitive performance may be expressed as ability and speed of learning, ability and speed of solving intellectual problems, ability to form and recall memories, reaction time, and the like. Cognition is understood as mental processes such as comprehension, inference, decision-making, planning, learning, memory, association, concept formation, language, attention, perception, action, problem solving and mental images. Cognitive decline may manifest as reduced memory; forgetfulness; word or name-finding problems; and/or decline in memory, concentration, ability to plan or organize, ability to perform complex tasks, and/or cognitive performance; and may result from age, stress, disease, or other grounds. Cognitive impairment may manifest in one or more of short-term memory loss, diminished capacity to learn, diminished rate of learning, or diminished attention.

The term "mood" refers to a state or quality of feeling (an emotional state) at a particular time. Moods differ from simple emotions in that they are less specific, less intense, and less likely to be triggered by a particular stimulus or event. Moods generally have either a positive or negative valence. An improved mood may comprise one or more of a decreased anxiety level, a decreased stress level, an increased perceived energy level, or a more positive emotional state.

With respect to dysphagia, a preferred embodiment of the composition administers a therapeutically effective amount of cuminaldehyde as a nutritional supplement, such as a nutrient-dense beverage. In another preferred embodiment for treatment of dysphagia, the therapeutically effective amount of cuminaldehyde is administered in a hydration supplement. Such supplements may be in the form of a thickened liquid. In yet another preferred embodiment for treatment of dysphagia, the therapeutically effective amount of cuminaldehyde is administered in a texture-modified food.

In an embodiment, the composition includes a prebiotic. The prebiotic may preferably be selected from the group consisting of acacia gum, alpha glucan, arabinogalactans, beta glucan, dextrans, fructooligosaccharides, fucosyllactose, galactooligosaccharides, galactomannans, gentiooligosaccharides, glucooligosaccharides, guar gum, inulin, isomaltooligosaccharides, lactoneotetraose, lactosucrose, lactulose, levan, malto dextrins, milk oligosaccharides, partially hydrolyzed guar gum, pecticoligosaccharides, resistant starches, retrograded starch, sialooligosaccharides, sialyllactose, soyoligosaccharides, sugar alcohols, xylooligosaccharides, their hydrolysates, and combinations thereof.

In an embodiment, the composition includes a probiotic. The probiotic may preferably be selected from the group consisting of *Aerococcus, Aspergillus, Bacteroides, Bifidobacterium, Candida, Clostridium, Debaromyces, Enterococcus, Fusobacterium, Lactobacillus, Lactococcus, Leuconostoc, Melissococcus, Micrococcus, Mucor, Oenococcus, Pediococcus, Penicillium, Peptostrepococcus, Pichia, Propionibacterium, Pseudocatenulatum, Rhizopus, Saccharomyces, Staphylococcus, Streptococcus, Torulopsis, Weissella*, and combinations thereof.

In an embodiment, the composition includes an amino acid. The amino acid may preferably be selected from the group consisting of alanine, arginine, asparagine, aspartate, citrulline, cysteine, glutamate, glutamine, glycine, histidine, hydroxyproline, hydroxyserine, hydroxytyrosine, hydroxylysine, isoleucine, leucine, lysine, methionine, phenylalanine, proline, serine, taurine, threonine, tryptophan, tyrosine, valine, and combinations thereof.

In an embodiment, the composition includes a fatty acid component, preferably a fish oil or a component thereof, which is preferably selected from the group consisting of docosahexaenoic acid ("DHA"), eicosapentaenoic acid ("EPA"), and combinations thereof. DHA and EPA may also be derived from krill, plant sources containing co-3 fatty acids, flaxseed, walnut, algae, and combinations thereof. Certain fatty acids (e.g. 18:4 fatty acids) may also be readily converted to DHA and/or EPA. The composition may include a-linolenic acid.

In an embodiment, the composition includes a phytonutrient. The phytonutrient may preferably be selected from flavonoids, allied phenolic compounds, polyphenolic compounds, terpenoids, alkaloids, sulphur-containing compounds, and combinations thereof, and in particular from the group consisting of carotenoids, plant sterols, quercetin, curcumin, limonin, and combinations thereof.

In an embodiment, the composition includes an antioxidant. The antioxidant may preferably selected from the group consisting of astaxanthin, carotenoids, coenzyme Q10 ("CoQ1O"), flavonoids, glutathione, Goji (wolfberry), hesperidin, lactowolfberry, lignan, lutein, lycopene, polyphenols, selenium, vitamin A, vitamin C, vitamin E, zeaxanthin, and combinations thereof.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating oral pharyngeal dysphagia comprising administering to an individual having the oral pharyngeal dysphagia a composition comprising a therapeutically effective amount of cuminaldehyde wherein the therapeutically effective amount of cuminaldehyde provokes a swallowing reflex and the cuminaldehyde is selected from the group consisting of isolated cuminaldehyde and synthetic cuminaldehyde.

2. The method of claim 1, wherein the composition is a thickened beverage.

3. The method of claim 1, wherein the cuminaldehyde is an isolated compound.

4. The method of claim 3, wherein the isolated compound is isolated from at least one source selected from the group consisting of: essential oils, cumin, cinnamon, bitter orange, and anise.

5. The method of claim 1, wherein the cuminaldehyde is administered as a nutritional supplement.

* * * * *